US011089999B1

(12) United States Patent
Williams

(10) Patent No.: US 11,089,999 B1
(45) Date of Patent: Aug. 17, 2021

(54) HYDRATION MEASUREMENT WITH A WATCH

(71) Applicant: Apple Inc., Cupertino, CA (US)

(72) Inventor: Alexander W. Williams, Santa Clara, CA (US)

(73) Assignee: Apple Inc., Cupertino, CA (US)

( * ) Notice: Subject to any disclaimer, the term of this patent is extended or adjusted under 35 U.S.C. 154(b) by 449 days.

(21) Appl. No.: 15/940,894

(22) Filed: Mar. 29, 2018

(51) Int. Cl.
*A61B 5/053* (2021.01)
*A61B 5/00* (2006.01)
*A61B 5/0531* (2021.01)
*A61B 5/0537* (2021.01)

(52) U.S. Cl.
CPC .......... *A61B 5/4875* (2013.01); *A61B 5/0531* (2013.01); *A61B 5/0537* (2013.01); *A61B 5/681* (2013.01); *A61B 5/6824* (2013.01); *A61B 5/742* (2013.01)

(58) Field of Classification Search
None
See application file for complete search history.

(56) References Cited

U.S. PATENT DOCUMENTS

| 9,510,778 | B2 | 12/2016 | Connolly | |
|---|---|---|---|---|
| 2005/0069925 | A1 | 3/2005 | Ford et al. | |
| 2016/0338639 | A1* | 11/2016 | Myers | A61B 5/681 |
| 2018/0344181 | A1* | 12/2018 | Schroeder | A61B 5/681 |
| 2019/0008448 | A1* | 1/2019 | Begtrup | G01N 33/48792 |

FOREIGN PATENT DOCUMENTS

WO WO-2017/058806 A1 4/2017

OTHER PUBLICATIONS

Liu et al., "Implementation of a Microfluidic Conductivity Sensor—a Potential Sweat Electrolyte Sensing System for Dehydration Detection," IEEE 2014, pp. 1678-1681.
Morgan et al., "Acute effects of dehydration on a sweat composition in men during prolonged exercise in the heat," Acta Physiol Scand, Sep. 2004, abstract only, retrieved from https://www.ncbi.nlm.nih.gov/pubmed/15329055, 2 pages.

* cited by examiner

*Primary Examiner* — Eric F Winakur
*Assistant Examiner* — Marjan Fardanesh
(74) *Attorney, Agent, or Firm* — Morgan, Lewis & Bockius LLP

(57) ABSTRACT

Hydration measurement capabilities can be provided by a wearable electronic device, such as a watch, to allow a user to easily track hydration. A watch can be positioned to receive and measure one or more electrical properties of perspiration produced by the user wearing the watch. The watch provides electrodes for measuring the electrical properties of the perspiration. The electrical properties, such as electrical conductance, can represent a concentration of electrolytes in the perspiration, which in turn represents a hydration level of the user. The hydration tracking can be performed non-invasively, repeatedly, accurately, automatically, and with minimal user intervention. The measurements can be used to provide useful feedback and health tracking information to a user, thereby allowing the user to better manage hydration and overall health.

19 Claims, 5 Drawing Sheets

HYDRATION MEASUREMENT WITH A WATCH

TECHNICAL FIELD

The present description relates generally to user hydration tracking, and, more particularly, to hydration measurement with a watch.

BACKGROUND

Portable electronic devices have become increasingly popular, and the features and functionality provided by portable electronic devices continue to expand to meet the needs and expectations of many consumers. However, some traditional portable electronic devices, particularly wearable electronic devices, may have relatively limited functionality or are only able to perform a specialized set of functions or tasks. For example, some traditional electronic wristwatches may be configured to perform a relatively limited set of functions, including displaying time, date, and performing basic timing functions. The embodiments described herein are directed to a wearable electronic device that provides a wide range of functionality, including hydration tracking for a user wearing the device.

BRIEF DESCRIPTION OF THE DRAWINGS

Certain features of the subject technology are set forth in the appended claims. However, for purpose of explanation, several embodiments of the subject technology are set forth in the following figures.

DETAILED DESCRIPTION

Figure 1:
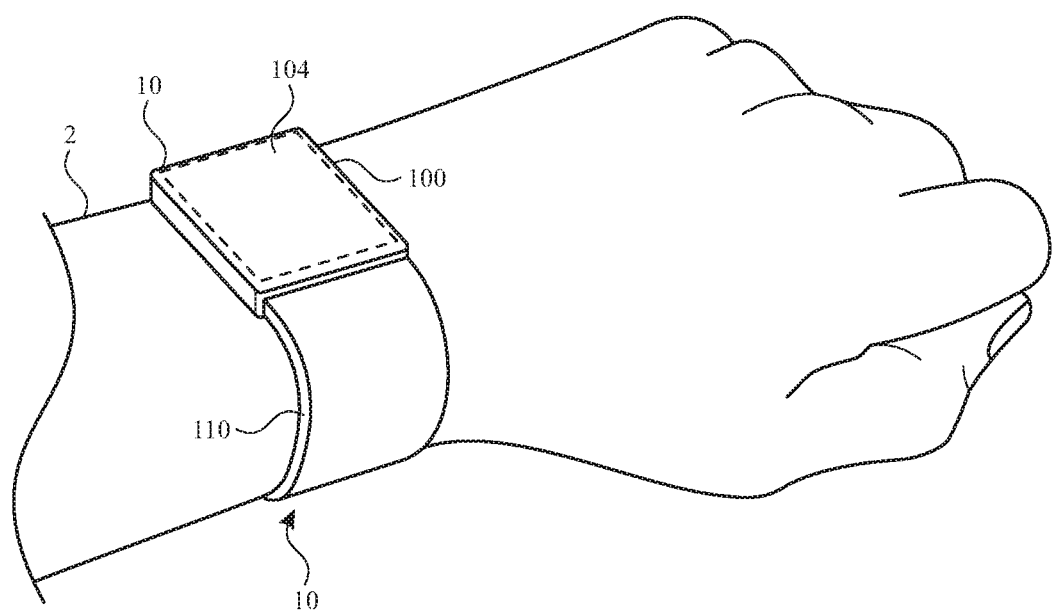
FIG. 1 illustrates a perspective view of a watch on a wrist of a user.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be clear and apparent to those skilled in the art that the subject technology is not limited to the specific details set forth herein and may be practiced without these specific details. In some instances, well-known structures and components are shown in block diagram form in order to avoid obscuring the concepts of the subject technology.

The following disclosure relates to user hydration tracking, and, more particularly, to hydration measurement with a watch. Hydration measurements can be used to provide useful information for automated and/or manual tracking of a user's activity and health.

Some portable electronic devices, such as watches, provide limited fitness and/or health tracking capabilities. Because these devices can be used during periods of user activity, fitness and/or health metrics can be helpful to protect the health and safety of the user during the activity. However, the type of information that can be obtained is limited by the capabilities of the electronic device. Some existing devices focus on tracking only certain metrics, such as movement and heartrate.

A user's hydration level has significant impacts on the health of a user. Dehydration can impair performance and is associated with several deleterious health consequences, including heat strokes. Overdrinking can result in hyponatremia, fatigue, confusion, coma, and even death.

Traditional techniques for tracking hydration are generally invasive, expensive, or unreliable. For example, some hydration tracking techniques involve testing fluid samples, such as urine or blood, from the user. Some techniques require analyte sensors to chemically react with sample fluids. Many of these sensors are disposable and limited to a single use. Yet other techniques involve tracking the intake of fluids, expulsion of fluids (e.g., sweat, urine, etc.), and weight changes across a period of time. These techniques are cumbersome and unreliable due to the variety of measurements that must be manually taken.

In contrast to traditional devices, the hydration measurement capabilities described herein provide reliable and elegant solutions that allow a user to easily track hydration with a wearable electronic device, such as a watch, and provide helpful feedback to the user to improve safety and health of the user during activities. In some embodiments of the present disclosure, hydration measurements can be achieved by a watch that also provides a variety of other capabilities, including tracking other activity and/or health metrics. Accordingly, hydration tracking can be provided as part of a comprehensive tracking system for conveniently providing accurate fitness and/or health information for a user.

In some embodiments of the present disclosure, hydration tracking can be performed repeatedly with the same equipment and without requiring disposable testing components that are exhausted after each use. Hydration tracking is performed non-invasively by sampling perspiration (e.g., sweat) that is produced by the user. For example, a watch is positioned to receive and measure one or more electrical properties of the perspiration and correlate the measurements with a concentration of electrolytes in the perspiration. The concentration of electrolytes can, in turn, be used to determine a hydration level of the user. For example, a high level of electrical conductance of the perspiration can indicate a high concentration of electrolytes and a low level of hydration. By further example, a low level of electrical conductance of the perspiration can indicate a low concentration of electrolytes and a high level of hydration. These measurement and calculations can be used to provide feedback and health tracking information to a user, for example, during an activity of the user.

These and other embodiments are discussed below with reference to FIGS. 1-11. However, those skilled in the art will readily appreciate that the detailed description given herein with respect to these figures is for explanatory purposes only and should not be construed as limiting.

According to some embodiments, for example as shown in FIG. 1, a watch 10 includes a watch body 100 that is worn on a wrist 2 with a watch band 110. The watch body 100 can be portable and also attached to other body parts of the user or to other devices, structures, or objects. The watch band 110 can be flexible and encircle at least a portion of the wrist 2 of a user. By securing the watch body 100 to the person of the user, the watch band 110 provides security and convenience. In some embodiments, the watch body 100 includes a display 104 and a housing for containing components.

Figure 2:
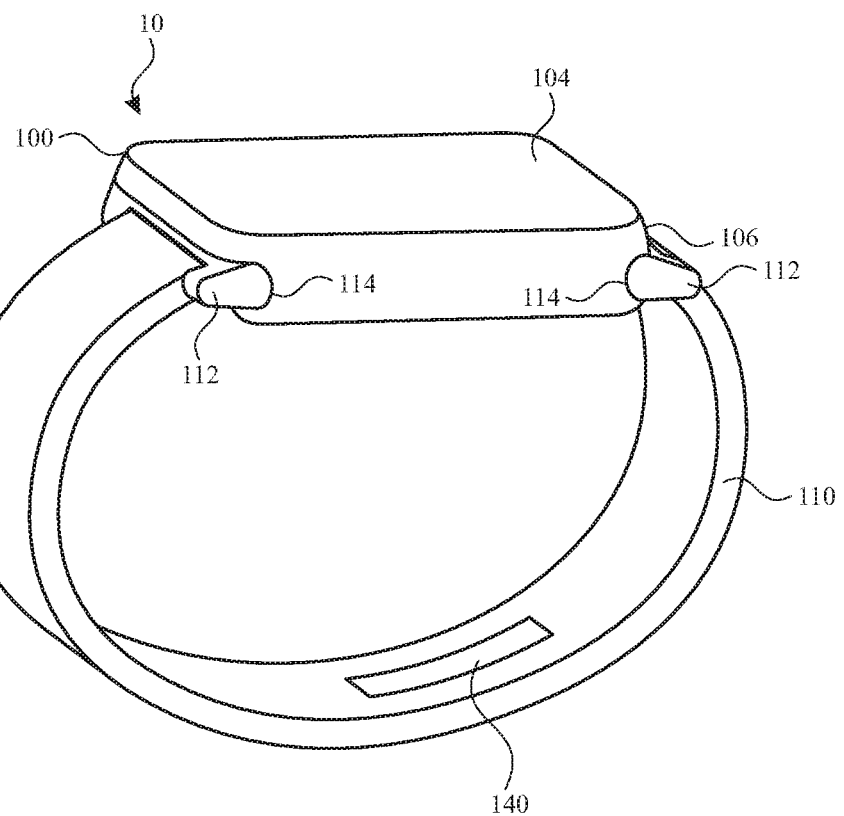
FIG. 2 illustrates a perspective view of an exemplary watch.

FIG. 2 illustrates a perspective view of the watch 10, including the watch body 100 and a watch band 110. As shown, the watch body 100 includes a housing 106 that supports the display 104. The watch body 100 can be worn on a user's wrist and secured thereto by the watch band 110. The watch band 110 can be a continuous structure or assembled as separate portions (e.g., straps) that join together and provide adjustable size configurations. The watch band 110 includes lugs 112 at opposing ends of the band that fit within respective recesses or channels 114 of the housing 106 and allow the watch band 110 to be removably attached to the housing 106. The lugs 112 may be part of the watch band 110 or may be separable (and/or separate) from the watch band 110. Generally, the lugs 112 may lock into the channels 114 and thereby maintain connection between the watch band 110 and the housing 106. The user may release a locking mechanism (not shown) to permit the lugs 112 to slide or otherwise move out of the channels 114. In some watches, the channels 114 may be formed in the watch band 110 and the lugs may be affixed or incorporated into the housing 106. While lugs 112 and channels 114 are illustrated, it will be recognized that other attachment elements, such as locks, snaps, clasps, threads, and pins can be included on the watch band 110 for securely attaching to the watch body 100.

As further shown in FIG. 2, the watch 10 can provide one or more electrodes 140 for measuring and/or otherwise responding to perspiration. For example, as shown in FIG. 2, electrodes 140 can be provided on an inner surface of the watch band 110. Alternatively or in combination, electrodes 140 can be provided on an inner surface of the watch body 100. The electrodes 140 can be positioned to come into contact with perspiration (e.g., sweat) that is present on the skin of the user. The electrodes 140 can be operated to measure an electrical property of the perspiration, from which hydration indicators can be determined and provided to a user. The electrodes 140 can be provided in or of a variety of arrangements, as discussed further herein.

Figure 3:
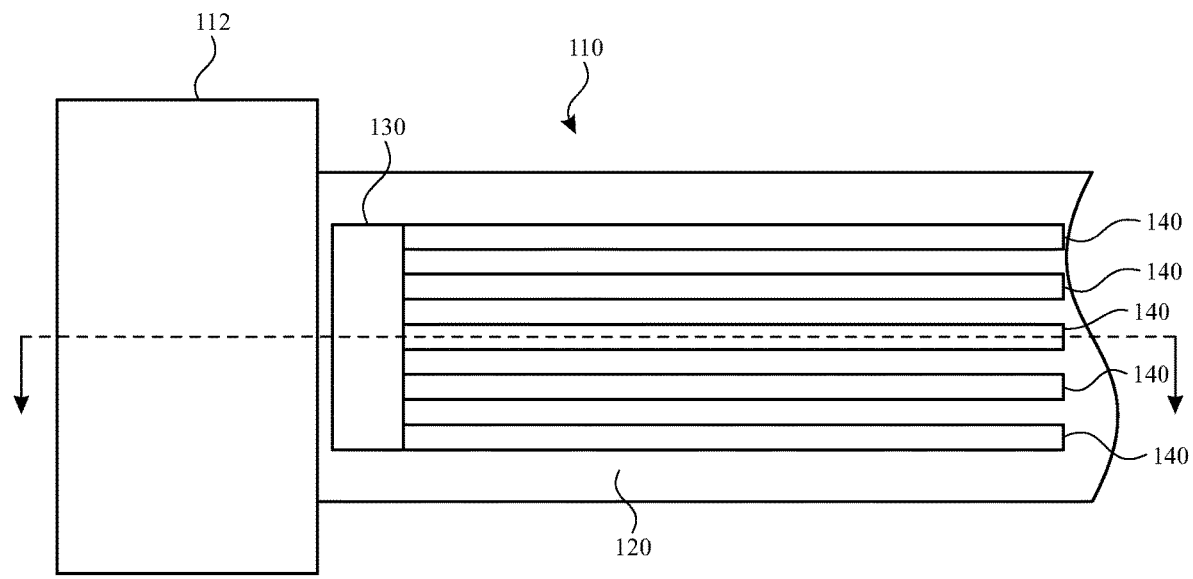
FIG. 3 illustrates a bottom view of an exemplary watch band.
Figure 4:
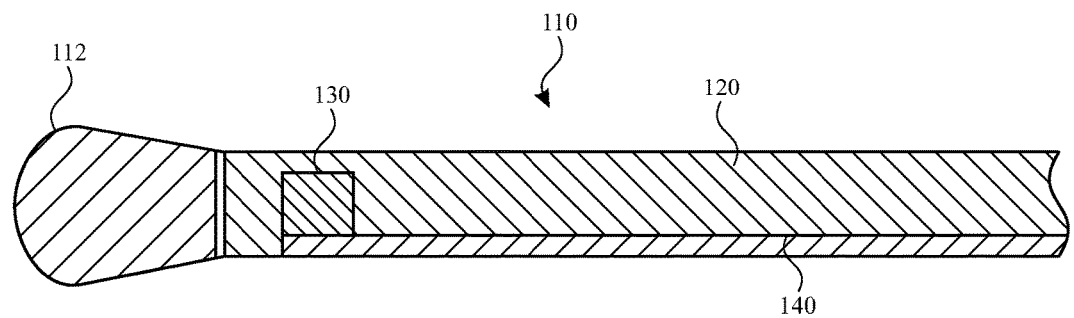
FIG. 4 illustrates a sectional view of the watch band of FIG. 3.

FIGS. 3 and 4 illustrate, respectively, a bottom view and a sectional view of an exemplary watch band 110. As shown, the watch band 110 includes a lug 112 for securely attaching to the watch body. The watch band 110 further includes a support structure 120 extending from the lug 112 along a longitudinal axis. The support structure 120 supports and/or houses one or more electrodes 140.

The watch band 110 can further include a meter 130 for performing operations with the electrodes 140. The meter 130 can perform measurements of electrical conductivity across any given pair of electrodes 140. When perspiration is provided across a given pair of electrodes 140, the electrodes 140 can act as probes to measure electrical properties of the perspiration with operations discussed further herein. The electrical properties can include electrical conductance, electrical conductivity, electrical resistance, and/or electrical resistivity. It will be appreciated that different electrical properties can be derived given sufficient known values. Where one of the above electrical properties is directly measured, others can be calculated. As used herein, measurement of electrical conductance can include measurement of a different electrical property and calculation of electrical conductance based on the measurement. As used herein, measurement of electrical conductance can include measurement of electrical conductance and calculation of a different electrical property based on the measurement. The support structure 120 can be electrically insulative to electrically isolate the electrodes 140 from each other. Accordingly, a circuit can be formed by the meter 130, the electrodes 140, and the perspiration.

The meter 130 can include or be connected to electronics to perform electrical measurements. The meter 130 can be positioned on and/or in the support structure 120 and/or the lug 112. The meter 130 can be independently connected to each of the electrodes 140. Accordingly, the meter 130 can controllably measure an electrical property across any given pair of the electrodes 140 (e.g., adjacent or non-adjacent). For example, the meter 130 can measure electrical conductance through perspiration between electrodes 140 by applying a current through the perspiration and measuring the voltage across the perspiration. These measurements can be used to calculate electrical conductance and/or electrical resistance with Ohm's Law. The meter 130 can include or be connected to electronics to communicate with the watch body and/or receive power from the watch body.

As shown in FIG. 3, the electrodes 140 can extend along a length of the support structure 120. Any given pair of the electrodes 140 (e.g., adjacent or non-adjacent) can extend parallel to each other at a fixed distance relative to each other. The longitudinal length of the electrodes 140 provides significant lengths for sampling, thereby providing measurement capabilities along a significant portion of the watch band 110. Accordingly, perspiration provided at any portion of the lengths of the electrodes 140 can be sampled and measured. The fixed distance provides a known constraint regarding the distance travelled by electrical current flowing from one electrode 140 to another electrode 140. Such a constraint can be used to calculate an electrical property (e.g., where conductance is a factor of length travelled through the perspiration). The electrodes 140 can maintain a gap of a fixed distance when the watch band 110 bends to wrap about an axis (i.e., "wrap axis") defined by the wrist of the user. For example, the gap can be oriented parallel to the wrap axis (e.g., wrist) so that the bending about the wrap axis does not change the size of the gap. Such consistency facilitates calculations that rely on a known gap size between electrodes.

Any number of electrodes 140 can be provided. At least two electrodes 140 can be provided for forming a circuit. By further example, more than two electrodes 140 can be provided. The watch can include 2, 3, 4, 5, 6, 7, 8, 9, 10, 11, 12, 13, 14, 15, 16, 17, 18, 19, 20, or more than 20 electrodes 140. The electrodes 140 can have the same or different characteristics, such as shape and size. Different pairs of electrodes 140 can be separated by the same or different distances (e.g., gap sizes).

Figure 5:
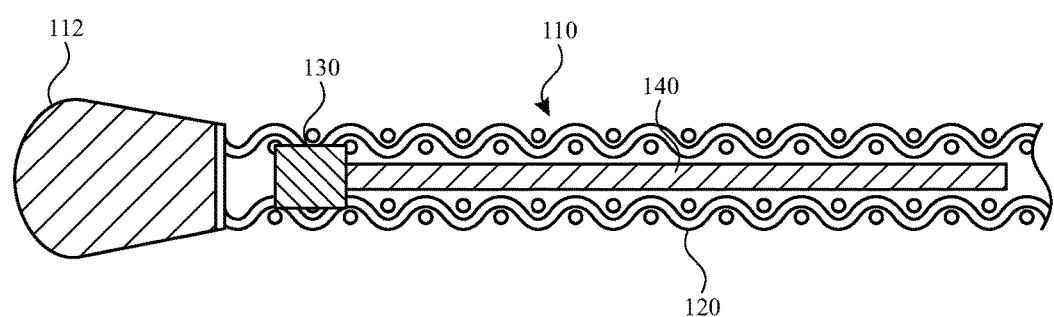
FIG. 5 illustrates a sectional view of an exemplary watch band.

FIG. 5 illustrates a sectional view of the watch band 110, in which with the support structure 120 is formed at least partially by woven, fabric threads. The woven threads can at least partially surround the meter 130 and/or the electrodes 140. For example, the woven threads can form an inner layer and/or an outer layer on opposing sides of the electrodes 140. The woven threads can include warp and weft threads and/or arranged in one or more of a variety of weave patterns. Multiple layers, including opposing layers, can be interwoven together. The electrodes 140 can be interwoven with the threads or simply embedded between layers of the support structure 120. Woven threads of the support structure 120 can be provided in an arrangement that at least partially exposes the electrodes 140 to perspiration from the skin of the user. For example, the woven threads can form interstitial spaces that wick perspiration away from the skin of the user and toward the electrodes 140. This can be accomplished, for example, by capillary action. This absorption provided by the threads facilitates measurement of the perspiration without requiring the electrodes 140 to be positioned on an outermost surface of the watch band 110. This arrangement provides protection to the electrodes 140 while maintaining measurement capabilities. The threads of the support structure 120 can be electrically insulative to electrically isolate the electrodes 140 from each other.

Figure 6:
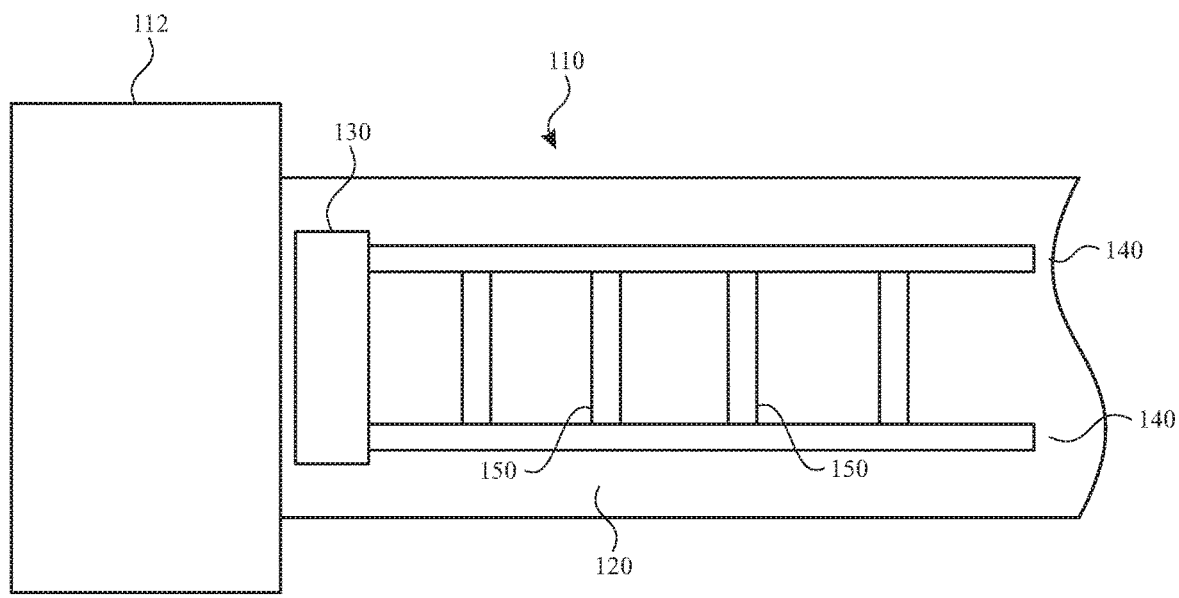
FIG. 6 illustrates a bottom view of an exemplary watch band.

FIG. 6 illustrates a bottom view of the watch band 110 with support members 150 between electrodes 140. The support members 150 can be provided between any pair of electrodes 140 to maintain a fixed distance (e.g., gap size) there between. The support members 150 can provide adequate rigidity and column strength to secure the electrodes 140 relative to each other. Where the electrodes 140 extend across a significant distance, multiple support members 150 can be provided. The support members 150 can be particularly beneficial where the support structure 120 provides less rigidity. For example, the support structure 120 can include a woven fabric or other soft material that loosely contains or supports the electrodes 140. In this arrangement, the support members 150 can be provided to adequately support the electrodes 140. The support members 150 can be electrically insulative to electrically isolate the electrodes 140 from each other.

Figure 7:
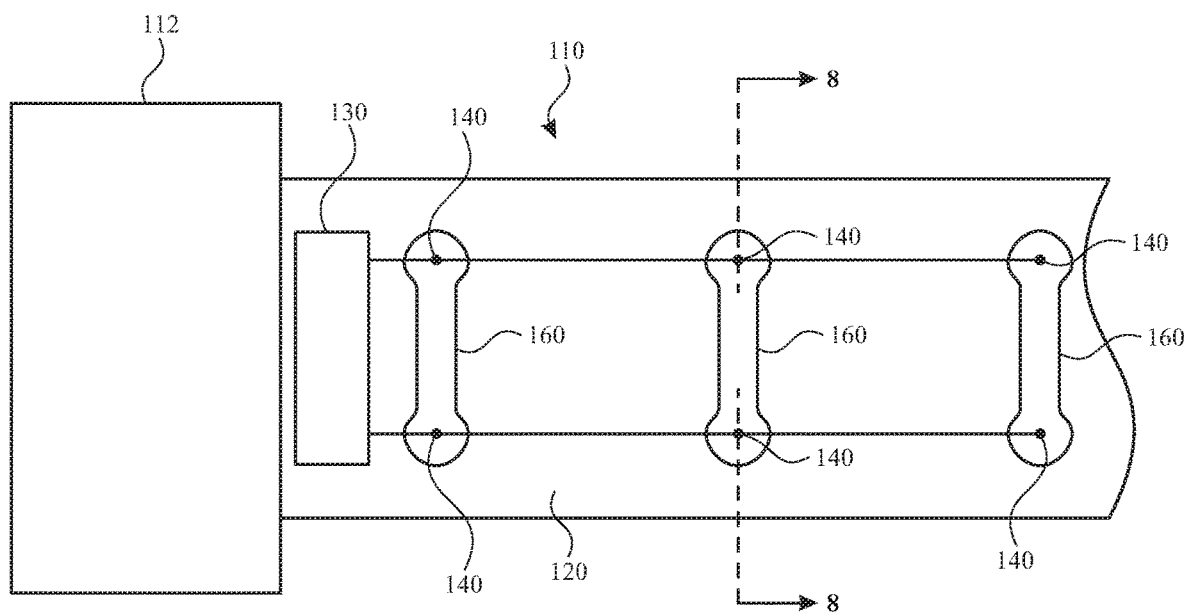
FIG. 7 illustrates a bottom view of an exemplary watch band.
Figure 8:
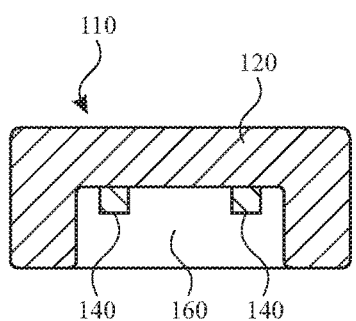
FIG. 8 illustrates a sectional view of the watch band of FIG. 7.

FIGS. 7 and 8 illustrate, respectively, a bottom view and a sectional view of the watch band 110 with the electrodes 140 positioned within cavities 160 formed in the support structure 120. The cavities 160 can each be recessed within the support structure 120 to form a space for receiving perspiration. This can be accomplished, for example, by capillary action to facilitate measurement of the perspiration without requiring the electrodes 140 to be positioned on an outermost surface of the watch band 110. The cavity 160 further provides known dimensions (e.g., height, width, length, volume) for a sample of perspiration. These known dimensions can be used to calculate electrical properties based on given measurements. Each cavity 160 can contain one or more electrodes 140. Multiple cavities 160 can be interconnected by channels, for example forming a mesh or network of cavities 160 in fluid communication with each other.

Other features of the support structure 120 and/or the electrodes 140 can facilitate sample acquisition and measurement. The support structure 120 and/or the electrodes 140 can include one or more surface features to facilitate drawing perspiration toward the electrodes 140. For example, the support structure 120 and/or the electrodes 140 can include a hydrophilic and/or hydrophobic coating. By further example, the support structure 120 and/or the electrodes 140 can include a surface texture that facilitates sample acquisition.

Combinations of and alterations to the above arrangements are contemplated. For example, different types of electrodes and electrode pairs can be included in the same watch band 110. Any number of electrodes and electrode pairs can be provided. Electrode pairs, across which electrical properties of perspiration is measured, can be separated by a gap that extends in any direction, including transverse to a longitudinal axis of the watch band 110 and/or parallel to a wrap axis of the watch band 110. Different electrode pairs can have different or the same gap orientations. Multiple electrode pairs can be distributed along a length and/or width of the watch band 110.

Figure 9:
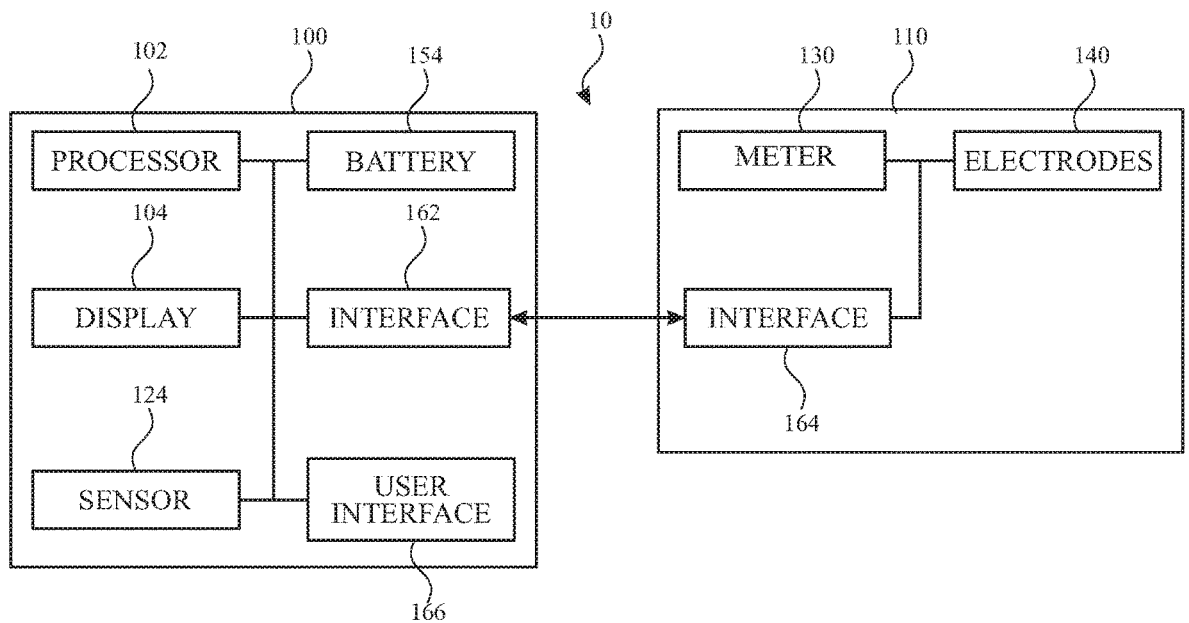
FIG. 9 illustrates a block system diagram of an exemplary watch.

FIG. 9 illustrates a block system diagram of an exemplary watch 10, including a watch body 100 and a watch band 110. The watch body 100 can include components for interacting with a user, the watch band 110, and/or another device. The watch body 100 can include components that facilitate hydration measurements.

As shown in FIG. 9, the watch body 100 can include components for interacting with a user. For example, the display 104 may provide an image or video output for the watch body 100. The display 104 may also provide an input surface for one or more input devices such as a touch sensing device, force sensing device, temperature sensing device, and/or a fingerprint sensor. The display 104 may be any size suitable for inclusion at least partially within the housing of the watch body 100 and may be positioned substantially anywhere on the watch body 100. The watch body 100 can further include one or more other user interfaces 166 for receiving input from and/or providing output to a user. For example, one or more buttons, dials, crowns, switches, or other devices can be provided for receiving input from a user. The user interface 166 can include a speaker, a microphone, and/or a haptic device. A haptic device can be implemented as any suitable device configured to provide force feedback, vibratory feedback, tactile sensations, and the like. For example, in one embodiment, the haptic device may be implemented as a linear actuator configured to provide a punctuated haptic feedback, such as a tap or a knock.

As further shown in FIG. 9, the watch body 100 includes one or more processing units 102 that include or are configured to access a memory having instructions stored thereon. The instructions or computer programs may be configured to perform one or more of the operations or functions described with respect to the watch 10. The processing units 102 can be implemented as any electronic device capable of processing, receiving, or transmitting data or instructions. For example, the processing units 102 may include one or more of: a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements. The memory can store electronic data that can be used by the watch body 100. For example, a memory can store electrical data or content such as, for example, audio and video files, documents and applications, device settings and user preferences, timing and control signals or data for the various modules, data structures or databases, and so on. The memory can be configured as any type of memory. By way of example only, the memory can be implemented as random access memory, read-only memory, Flash memory, removable memory, or other types of storage elements, or combinations of such devices.

As further shown in FIG. 9, the watch body 100 may include a battery 154 that is used to store and provide power to the other components of the watch body 100. The battery 154 may be a rechargeable power supply that is configured to provide power to the watch body 100 and/or the watch band 110 while being worn by the user. The watch body 100 may also be configured to recharge the battery 154 using a wireless charging system.

As further shown in FIG. 9, the watch body 100 may include a watch body interface 162 that facilitates transmission of data and/or power to or from other electronic devices across standardized or proprietary protocols. For example, a watch body interface 162 can transmit electronic signals via a wireless and/or wired network connection. Examples of wireless and wired network connections include, but are not limited to, cellular, Wi-Fi, Bluetooth, infrared, RFID and Ethernet. The watch body interface 162 can communicate with or sense the watch band 110 via a watch band interface 164 of the watch band 110.

As further shown in FIG. 9, the watch body 100 may also include one or more biosensors 124 positioned substantially anywhere on the watch body 100. The one or more biosensors 124 may be configured to sense substantially any type of characteristic such as, but not limited to, images, pressure, light, touch, force, temperature, position, motion, and so on. For example, the sensor(s) 124 may be a photodetector, a temperature sensor, a light or optical sensor, an atmospheric pressure sensor, a humidity sensor, a magnet, a gyroscope, an accelerometer, and so on. In other examples, the watch body 100 may include one or more health sensors. In some examples, the health sensors can be disposed on a bottom surface of the housing of the watch body 100. The one or more biosensors 124 can include optical and/or electronic biometric sensors that may be used to compute one or more health metrics. A biosensor 124 can include a light source and a photodetector to form a photoplethysmography (PPG) sensor. The optical (e.g., PPG) sensor or sensors may be used to compute various health metrics including, without limitation, a heart rate, a respiration rate, blood oxygenation level, a blood volume estimate, blood pressure, or a combination thereof. One or more of the biosensors 124 may also be configured to perform an electrical measurement using one or more electrodes. The electrical sensor(s) may be used to measure electrocardiographic (ECG) characteristics, galvanic skin resistance, and other electrical properties of the user's body. Additionally or alternatively, a biosensor 124 can be configured to measure body temperature, exposure to UV radiation, and other health-related information.

As further shown in FIG. 9, the watch band 110 can include a watch band interface 164, a meter 130, and electrodes 140, as discussed herein. The meter 130 can operate with the electrodes 140 to obtain hydration measurements. The meter 130 can perform operations based on commands generated by the processor 102 and communicated via the watch body interface 162 and the watch band interface 164. Alternatively or additionally, the meter 130 can operate autonomously without commands generated by any component of the watch body 100.

It will be recognized that one, some, or all of the components of the watch body 100 of FIG. 9 can be provided, alternatively or additionally, on and/or within the watch band 110 of the watch 10. For example, a processing unit 102, a display 104, a sensor 124, a battery 154, a watch body interface 162, and/or a user interface 166 can be provide on the watch body 100 and/or the watch band 110. It will be further recognized that one, some, or all of the components of the watch band 110 of FIG. 9 can be provided, alternatively or additionally, on and/or within the watch body 100 of the watch 10. For example, a meter 130, an electrode 140, and/or a watch band interface 164 can be provide on the watch band 110 and/or the watch body 100.

Methods of tracking user hydration are provided herein. The methods can apply one or more aspects of the design arrangements discussed herein with respect to a watch.

Figure 10:
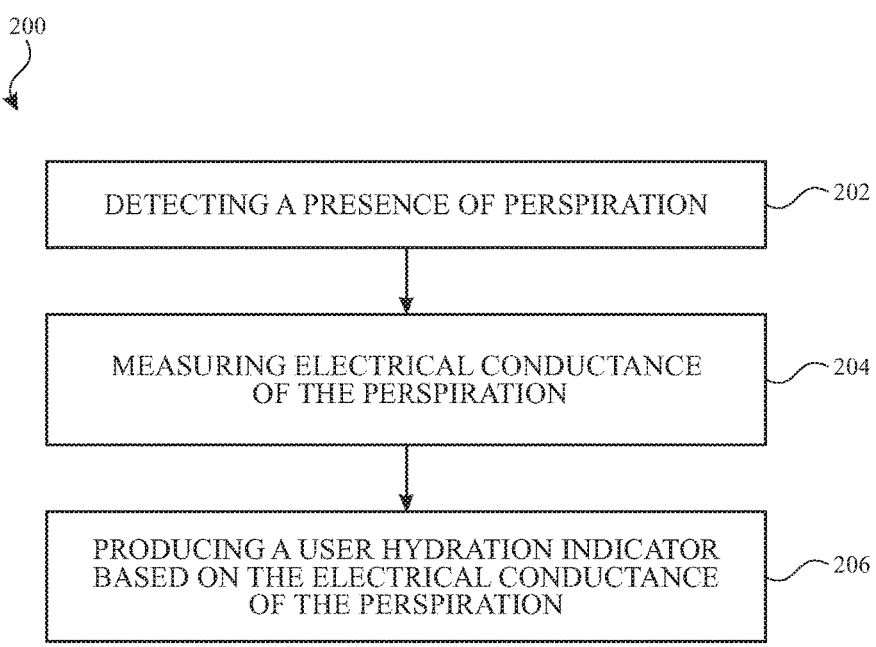
FIG. 10 illustrates a flow chart of an exemplary process.

FIG. 10 illustrates an exemplary method 200 for tracking user hydration. In operation 202, a watch detects a presence of perspiration between electrodes of the watch. The detection can be automated, passive, or based on an express command. The detection can be based on a detectable level of conductance between multiple electrodes, for example where such conductance is not present in the absence of a fluid, such as perspiration. The detection can also be initiated based on activity (e.g., motion) of the user and/or initiation of a fitness tracking program of the watch. A polling operation can be performed in which various electrode pairs are tested to determine the presence of perspiration. Where perspiration is detected (e.g., via relatively high conductance) across fewer than every pair of electrodes, further measurements can be limited to only those electrode pairs that are determined to be bridged by perspiration. Electrode pairs that are determined not to be bridged by perspiration can be omitted from at least some further measurements.

In operation 204, the watch measures an electrical conductance of the perspiration between the electrodes. For example, electrical conductance can be measured through perspiration between the electrodes by applying a fixed current through the perspiration and measuring the voltage across the perspiration. Alternatively or additionally, electrical conductance of the perspiration can be measured by applying a fixed voltage across the perspiration and measuring the current through the perspiration. These measurements can be used to calculate electrical conductance and/or electrical resistance with Ohm's Law. It will be recognized that other techniques can be applied to measure electrical conductance. For example, a precision ohmmeter can take measurements with Kelvin sensing, for example with four electrodes (e.g., Kelvin contacts). Two of the electrodes can carry the current to and from the meter, while the other two electrodes allow the meter to measure the voltage across the perspiration. In this arrangement, the power source is connected in series with the perspiration to be measured through the first pair of electrodes, while the second pair of electrodes connects, in parallel, a galvanometer which measures the voltage drop. With this type of meter, any voltage drop due to the resistance of the first pair of electrodes and their contact resistances is ignored by the meter.

It will be appreciated that different electrical properties can be derived given sufficient known values. For example, electrical conductance and electrical resistance are inversely related, and electrical conductivity and electrical resistivity are inversely related. By further example, electrical conductivity and electrical resistivity can be calculated based on electrical conductance and/or electrical resistance as well as other known properties of the perspiration, such as geometric properties of the sample thereof. Where multiple electrode pairs are available for measuring, final measurements can be based on a combination (e.g., average, sum, etc.) of initial measurements across each of the multiple electrode pairs. Filters can be applied, for example, to exclude outliers in a set of measurements across multiple electrode pairs.

In operation 206, the watch produces a user hydration indicator based on the electrical conductance of the perspiration. The user hydration indicator can be based on a correlation of the measured electrical conductance with electrolyte concentration of the perspiration, which is in turn correlated with the hydration level of the user. Because higher concentration of electrolytes increases conductance, and low user hydration yields high concentrations of electrolytes, a relatively higher conductance indicates lower hydration. Conversely, because lower concentration of electrolytes decreases conductance, and high user hydration yields low concentrations of electrolytes, a relatively lower conductance indicates higher hydration. Accordingly, the generation of a user hydration indicator can be based on the measured electrical conductance of the perspiration. The relationship between the measured electrical conductance and the user hydration indicator can be determined by a mathematical formula, a stored lookup table, and/or population studies. The user hydration indicator can include a hydration level, a change in hydration over a period of time, a hydration trend, a hydration trajectory, and/or a hydration prediction.

The watch can provide information to a user as an output based on the calculated user hydration indicator. The watch can provide such information via a display or another user interface, as discussed herein. The user hydration indicator can be provided to indicate a past, present, and/or future status of the user's hydration level. The user hydration indicator can be provided as an amount of fluid lost during an activity or over a period of time. The user hydration indicator can be provided along with other information (e.g., duration, heartrate, calories used) relating to a given activity. The user hydration indicator can be provided as or with a recommendation regarding an amount of fluid that is to be ingested by the user to restore a target hydration level. The user hydration indicator can be provided as a notification or alert when the user hydration indicator reaches or exceeds a threshold hydration level. Target and/or threshold hydration levels can be determined based on a stored lookup table and/or population studies. The watch can track and/or provide an ability for the user to input fluid intake to restore a hydration level. The watch can provide reminders and/or reports based on the user hydration indicator and/or the fluid intake. For example, the watch can track progress toward a target hydration level. The watch can provide periodic reminders over a duration of time based on a target fluid intake following a measured loss of hydration during a user activity.

Figure 11:
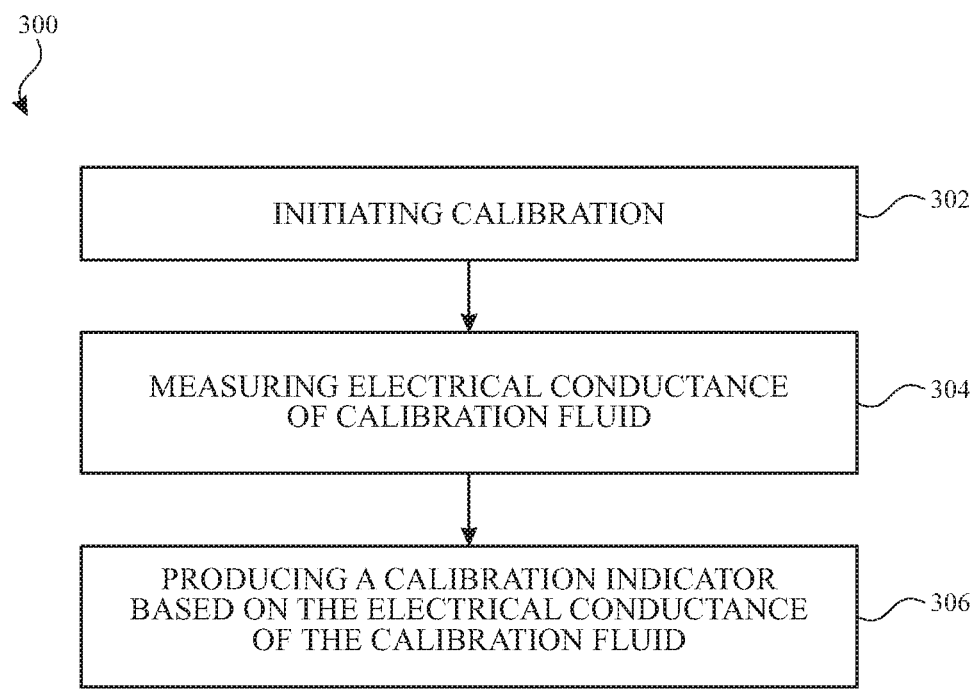
FIG. 11 illustrates a flow chart of an exemplary process.

FIG. 11 illustrates an exemplary method 300 for calibrating a hydration tracking system or a watch. In operation 302, a calibration stage is initiated, for example by the watch or by a user operating the watch. In operation 304, the watch measures an electrical conductance of a calibration fluid. For example, the user can immerse the electrodes in a fluid (e.g., tap water, distilled water) having a known electrical conductance. In operation 306, the watch produces a calibration indicator based on the electrical conductance of the calibration fluid. The calibration indicator can be compared to the known electrical conductance of the calibration fluid. Any offset or disparity between the calibration indicator and the known electrical conductance of the calibration fluid can be used to adjust subsequent calculations of a user hydration indicator based on measured electrical conductance of perspiration.

Therefore, the embodiments of the present disclosure provide reliable and elegant solutions that allow a user to easily track hydration with a wearable electronic device, such as a watch. As shown, hydration tracking can be performed non-invasively, repeatedly, accurately, automatically, and with minimal user intervention. The measurements and calculations can be used to provide useful feedback and health tracking information to a user, thereby allowing the user to better manage hydration and overall health.

To illustrate the interchangeability of hardware and software, items such as the various illustrative blocks, modules, components, methods, operations, instructions, and algorithms have been described generally in terms of their functionality. Whether such functionality is implemented as hardware, software or a combination of hardware and software depends upon the particular application and design constraints imposed on the overall system. Skilled artisans may implement the described functionality in varying ways for each particular application.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order.

It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

What is claimed is:

1. A watch comprising:
    a watch body;
    a watch band comprising a support structure for contacting skin of a user;
    electrodes positioned within the support structure of the watch band, such that the electrodes do not contact the skin of the user when the watch is worn by the user; and
    a meter operatively coupled to the electrodes to measure electrical conductance of a fluid in contact with the watch band.

2. The watch of claim 1, wherein:
    the watch body comprises:
        a channel; and
        a body interface positioned in the channel and being operatively connected to the meter; and
    the watch band comprises:
        a lug configured to secure the watch band to the watch body while the lug is within the channel; and
        a band interface configured to communicatively couple to the body interface when the lug is within the channel.

3. The watch of claim 1, further comprising a processing unit operable to
    produce a user hydration indicator based on the measured electrical conductance of the fluid, wherein the watch body comprises a user interface configured to output the user hydration indicator to the user wearing the watch.

4. The watch of claim 3, wherein:
    the electrodes comprise multiple electrode pairs; and
    the processing unit is configured to produce the user hydration indicator by averaging electrical conductance measurements from different electrode pairs.

5. The watch of claim 1, wherein the watch body further comprises a sensor configured to measure a health metric of the user wearing the watch.

6. A watch band comprising:
    a support structure forming a surface and a cavity recessed from the surface;
    electrodes positioned within the cavity and being recessed from the surface to be a distance away from skin of a user when the watch band is worn, the electrodes being responsive to perspiration from the skin of the user when the perspiration is within the cavity; and
    a band interface for communicating with a watch body of a watch.

7. The watch band of claim 6, further comprising a lug configured to attach to the watch body of the watch, wherein the band interface is configured to communicatively couple to a body interface of the watch body when the lug is attached to the watch body.

8. The watch band of claim 6, wherein the electrodes extend in parallel along a longitudinal length of the support structure.

9. The watch band of claim 6, wherein the watch band is configured to bend about an axis to conform to a wrist of the user, and a pair of the electrodes are separated by a gap that is oriented parallel to the axis.

10. The watch band of claim 6, further comprising support members to maintain an adjacent pair of the electrodes a fixed distance away from each other.

11. The watch band of claim 6, wherein the support structure comprises multiple threads that are electrically insulative and woven together around the electrodes.

12. The watch band of claim 6, wherein the electrodes comprise at least four electrodes.

13. The watch of claim 6, wherein the support structure forms a channel configured to direct the perspiration from the skin to the electrodes.

14. A method of tracking user hydration, the method comprising:
    detecting, with electrodes of a watch, a presence of perspiration between the electrodes, the watch comprising:

a watch body;

a watch band comprising a support structure for contacting skin of a user;

electrodes positioned within the support structure of the watch band, such that the electrodes do not contact the skin of the user when the watch is worn by the user; and a meter operatively coupled to the electrodes to measure electrical conductance of the perspiration in contact with the watch band;

measuring the electrical conductance of the perspiration between the electrodes; and producing a user hydration indicator based on the electrical conductance of the perspiration.

15. The method of claim 14, wherein:

the electrical conductance is a first electrical conductance;

the method further comprises, after measuring the first electrical conductance, measuring a second electrical conductance of the perspiration between the electrodes; and producing the user hydration indicator is based on a comparison between the first electrical conductance and the second electrical conductance.

16. The method of claim 14, wherein the method is performed upon detecting activity of the user with a sensor of the watch.

17. The method of claim 14, further comprising:

initiating a calibration stage;

measuring an electrical conductance of a calibration fluid; and producing a calibration indicator based on the electrical conductance of the calibration fluid.

18. The method of claim 17, wherein producing the user hydration indicator comprises comparing the electrical conductance of the perspiration to the electrical conductance of the calibration fluid.

19. The method of claim 14, wherein:

the electrodes comprise multiple electrode pairs; and producing the user hydration indicator is based on a combination of electrical conductance measurements from different electrode pairs.

* * * * *